US008734514B2

(12) United States Patent
Vargas et al.

(10) Patent No.: US 8,734,514 B2
(45) Date of Patent: May 27, 2014

(54) MICRO-ALLOYED POROUS METAL HAVING OPTIMIZED CHEMICAL COMPOSITION AND METHOD OF MANUFACTURING THE SAME

(75) Inventors: Joseph R. Vargas, Garnerville, NY (US); Steven J. Seelman, Montclair, NJ (US)

(73) Assignee: Zimmer, Inc., Warsaw, IN (US)

( * ) Notice: Subject to any disclaimer, the term of this patent is extended or adjusted under 35 U.S.C. 154(b) by 41 days.

(21) Appl. No.: 13/523,187

(22) Filed: Jun. 14, 2012

(65) Prior Publication Data
US 2012/0323323 A1 Dec. 20, 2012

Related U.S. Application Data

(60) Provisional application No. 61/497,780, filed on Jun. 16, 2011.

(51) Int. Cl.
*A61F 2/28* (2006.01)
*A61F 2/02* (2006.01)

(52) U.S. Cl.
USPC .................................. 623/11.11; 623/16.11

(58) Field of Classification Search
CPC ....................................................... A61F 2/28
USPC ........ 623/11.11, 16.11, 18.11; 427/2.24–2.27
See application file for complete search history.

(56) References Cited

U.S. PATENT DOCUMENTS

| 4,138,512 A | 2/1979 | Glaski |
| RE30,626 E | 5/1981 | Kaplan |
| 4,699,082 A | 10/1987 | Hakim |
| 4,821,674 A | 4/1989 | deBoer et al. |
| 4,996,942 A | 3/1991 | deBoer et al. |
| 5,102,694 A | 4/1992 | Taylor et al. |
| 5,154,970 A | 10/1992 | Kaplan et al. |
| 5,169,685 A | 12/1992 | Woodruff et al. |
| 5,198,034 A | 3/1993 | deBoer et al. |
| 5,282,861 A | 2/1994 | Kaplan |
| 5,283,109 A | 2/1994 | Kaplan et al. |
| 5,306,666 A | 4/1994 | Izumi |
| 5,374,315 A | 12/1994 | deBoer et al. |
| 5,427,620 A | 6/1995 | deBoer et al. |
| 5,427,631 A | 6/1995 | Johnsson et al. |

(Continued)

FOREIGN PATENT DOCUMENTS

| EP | 1927325 A1 | 6/2008 |
| WO | WO99/56800 A1 | 11/1999 |
| WO | WO-2012174211 A1 | 12/2012 |

OTHER PUBLICATIONS

"Experimental and clinical performance of porous tantalum in orthopedic surgery", Brett Levin et al., Biomaterials Bolumn 27, Issue 27, Sep. 2006, pp. 4671-4681—Abstract.

(Continued)

*Primary Examiner* — Jason-Dennis Stewart
(74) *Attorney, Agent, or Firm* — Schwegman Lundberg & Woessner, P.A.

(57) ABSTRACT

A micro-alloyed porous metal is disclosed having an optimized chemical composition to achieve targeted mechanical properties for use as an orthopaedic implant and a cell/soft tissue receptor. The porous metal may achieve a targeted compressive strength and a targeted ductility, for example. These targeted mechanical properties may allow the porous metal to be densified to a low relative density.

22 Claims, 4 Drawing Sheets

(56) References Cited

U.S. PATENT DOCUMENTS

| | | | |
|---|---|---|---|
| 5,443,515 | A | 8/1995 | Vohen et al. |
| 5,443,647 | A | 8/1995 | Aucoin et al. |
| 5,574,247 | A | 11/1996 | Nishitani et al. |
| 5,577,263 | A | 11/1996 | West |
| 5,755,809 | A | 5/1998 | Cohen et al. |
| 5,780,157 | A | 7/1998 | Tuffias et al. |
| 5,840,366 | A | 11/1998 | Mizuno et al. |
| 5,874,131 | A | 2/1999 | Vaarstra et al. |
| 5,876,793 | A | 3/1999 | Sherman et al. |
| 5,902,407 | A | 5/1999 | deBoer et al. |
| 5,919,531 | A | 7/1999 | Arkles et al. |
| 6,063,442 | A | 5/2000 | Cohen et al. |
| 6,352,594 | B2 | 3/2002 | Cook et al. |
| 6,641,918 | B1 | 11/2003 | Sherman et al. |
| 6,770,146 | B2 | 8/2004 | Koren et al. |
| 6,797,340 | B2 | 9/2004 | Fang et al. |
| 6,833,161 | B2 | 12/2004 | Wang et al. |
| 6,878,395 | B2 | 4/2005 | Kaeppeler |
| 6,949,273 | B2 | 9/2005 | Sharan |
| 7,368,018 | B2 | 5/2008 | Yamaguchi |
| 7,374,941 | B2 | 5/2008 | Bondestam et al. |
| 7,479,301 | B2 | 1/2009 | Eriksen |
| 7,485,340 | B2 | 2/2009 | Elers et al. |
| 7,601,393 | B2 | 10/2009 | Chiang et al. |
| 2002/0162500 | A1 | 11/2002 | Hong et al. |
| 2002/0197403 | A1 | 12/2002 | Arkles et al. |
| 2005/0011457 | A1 | 1/2005 | Chiang et al. |
| 2006/0110534 | A1 | 5/2006 | Hwang et al. |
| 2008/0096369 | A1 | 4/2008 | Strzyzewski et al. |
| 2008/0296660 | A1 | 12/2008 | Park et al. |
| 2008/0317954 | A1 | 12/2008 | Lu et al. |
| 2009/0107404 | A1 | 4/2009 | Ogliari et al. |
| 2009/0205563 | A1 | 8/2009 | Arena et al. |
| 2009/0214786 | A1 | 8/2009 | Chang et al. |
| 2009/0232983 | A1 | 9/2009 | Ammerlaan et al. |
| 2009/0288604 | A1 | 11/2009 | Kim et al. |
| 2010/0075419 | A1* | 3/2010 | Inagaki et al. ............... 435/402 |
| 2010/0080935 | A1* | 4/2010 | Brice .......................... 427/597 |
| 2013/0096667 | A1* | 4/2013 | Bregulla et al. ............. 623/1.15 |

OTHER PUBLICATIONS

"Chemical Vapor Deposition by Pulsed Ultrasonic Direct Injection of Liquid Precursors Produces Versatile Method for Creation of thin Film Circuits and Devices", Mark Leiby, Materials Research Society, URL: http://www.mrs.org/s_mrs/sec_subscribe.asp?CID=2505&DID=135969&action=detail.

Formability of Porous Tantalum Sheet-Metal, Nebosky et al., IOP Publishing 2009, Materials Science and Engineering 4 (2009).

RD521048A, Sep. 10, 2007.

Tantaline Technologies, Engineered Tantalum Products, accessed Jan. 26, 2010, URL: http://www.tantalum-coating.com/ProdEng.htm.

Azom.com, Boron Nitride (BN) Supplier Data by Goodfellow, accessed Jan. 27, 2010, URL: http://www.azom.com/Details.asp?ArticleID=2253.

"True to Foam", Paul Everitt, Jan. 2008, www.ceramicindustry.com.

Goodfellow Press Release Sep. 2008, Reticulated Foams.

TCH600 Nitrogen/Oxygen/Hydrogen Series, 2010 LECO Corporation.

"International Application Serial No. PCT/US2012/042410, International Preliminary Report on Patentability mailed Jan. 3, 2014", 9 pgs.

"International Application Serial No. PCT/US2012/042410, International Search Report and Written Opinion mailed Aug. 6, 2012", 14 pgs.

Zardiackas, Lyle D, et al., "Structure, metallurgy, and mechanical properties of porous tantalum foam", Journal of Biomedical Materials Research, vol. 58, No. 2, (Feb. 1, 2001), 180-187.

\* cited by examiner

MICRO-ALLOYED POROUS METAL HAVING OPTIMIZED CHEMICAL COMPOSITION AND METHOD OF MANUFACTURING THE SAME

CROSS REFERENCE TO RELATED APPLICATION

This application claims priority from U.S. Provisional Patent Application Ser. No. 61/497,780, filed Jun. 16, 2011, the disclosure of which is hereby expressly incorporated by reference herein in its entirety.

FIELD OF THE DISCLOSURE

The present disclosure relates to a porous metal for use as an orthopaedic implant. More particularly, the present disclosure relates to a micro-alloyed porous metal having an optimized chemical composition to achieve targeted mechanical properties for use as an orthopaedic implant, and to a method for manufacturing the same.

BACKGROUND OF THE DISCLOSURE

Orthopaedic implants may be constructed of porous metal to encourage bone growth into the orthopaedic implant. An example of such a material is produced using Trabecular Metal™ technology generally available from Zimmer, Inc., of Warsaw, Ind. Trabecular Metal™ is a trademark of Zimmer, Inc. Such a material may be formed from a reticulated vitreous carbon (RVC) foam substrate which is infiltrated and coated with a biocompatible metal in the manner disclosed in detail in U.S. Pat. No. 5,282,861 to Kaplan, the entire disclosure of which is expressly incorporated herein by reference. The resulting infiltrated and coated material is lightweight, strong, and has open cells that are similar to the structure of natural cancellous bone, thereby providing a matrix into which cancellous bone may grow to fix the orthopaedic implant to the patient's bone. The coated metal layer of the material may contain up to 2,000 ppm oxygen, up to 2,000 ppm nitrogen, and up to 500 ppm hydrogen. However, to achieve desired mechanical properties with this coated metal layer, the material is densified to a relative density of 18% or more, such as from 18% to 25%.

SUMMARY

The present disclosure relates to a micro-alloyed porous metal having an optimized chemical composition to achieve targeted mechanical properties for use as an orthopaedic implant and a cell/soft tissue receptor, and to a method for manufacturing the same. The porous metal may achieve a targeted compressive strength (e.g., 24,000 psi or more) and a targeted ductility (e.g., 50% or more), for example. These targeted mechanical properties may allow the porous metal to be densified to a lower relative density than is currently manufactured commercially. For example, the porous metal may be densified to a relative density less than 18%.

According to an embodiment of the present disclosure, a highly porous biomaterial is provided that is configured to be implanted in a patient's body. The highly porous biomaterial includes a porous substrate having a plurality of ligaments that define pores of the porous substrate and a biocompatible metal coating applied to the plurality of ligaments of the porous substrate, the highly porous biomaterial having a relative density less than 18%, the relative density being a percentage obtained by dividing an actual density of the highly porous biomaterial by a theoretical density of the biocompatible metal of the coating.

According to another embodiment of the present disclosure, a method is provided for manufacturing a highly porous biomaterial. The method includes the steps of: providing a porous substrate having a plurality of ligaments that define pores of the porous substrate; depositing a biocompatible metal coating onto the plurality of ligaments of the porous substrate; and setting at least one of a maximum oxygen concentration in the metal coating at 1,212 ppm, and a maximum nitrogen concentration in the metal coating at 1,243 ppm.

According to yet another embodiment of the present disclosure, a method is provided for manufacturing a highly porous biomaterial. The method includes the steps of: providing a porous substrate having a plurality of ligaments that define pores of the porous substrate; depositing a biocompatible metal coating onto the plurality of ligaments of the porous substrate; and setting a minimum nitrogen concentration in the metal coating at 488 ppm.

According to yet another embodiment of the present disclosure, a method is provided for manufacturing a highly porous biomaterial. The method includes the steps of: providing a porous substrate having a plurality of ligaments that define pores of the porous substrate; and depositing a biocompatible metal coating onto the plurality of ligaments of the porous substrate to a completed extent, the highly porous biomaterial having a relative density less than 18% at the completed extent, the relative density being a percentage obtained by dividing an actual density of the highly porous biomaterial by a theoretical density of the biocompatible metal of the coating.

BRIEF DESCRIPTION OF THE DRAWINGS

The above-mentioned and other features and advantages of this disclosure, and the manner of attaining them, will become more apparent and the invention itself will be better understood by reference to the following description of embodiments of the invention taken in conjunction with the accompanying drawings, wherein.

Corresponding reference characters indicate corresponding parts throughout the several views. The exemplifications set out herein illustrate exemplary embodiments of the invention and such exemplifications are not to be construed as limiting the scope of the invention in any manner.

DETAILED DESCRIPTION

Figure 1:
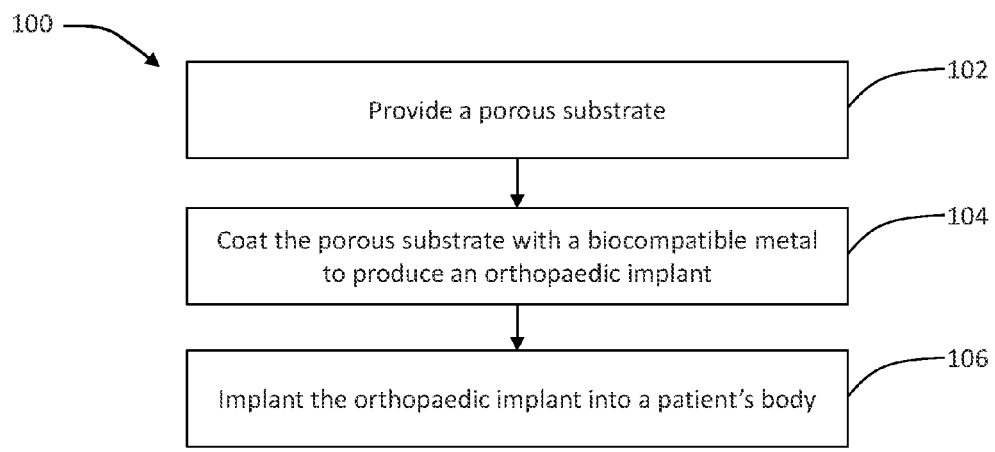
FIG. 1 is a flow diagram of an exemplary method of the present disclosure.

FIG. 1 provides an exemplary method 100 for manufacturing a micro-alloyed porous metal having an optimized chemical composition to achieve targeted mechanical properties for use as an orthopaedic implant and a cell/soft tissue receptor.

Beginning at step 102 of method 100 (FIG. 1), a porous lattice or substrate is provided having a large plurality of ligaments that define open-cells or pores therebetween. An exemplary porous substrate is a RVC foam substrate having a large plurality of vitreous carbon ligaments that define dodecahedron (12-sided) pores therebetween. RVC foam is commercially available in porosities ranging from 10 to 200 pores per inch, and more specifically in porosities of 65, 80, and 100 pores per inch. Such RVC foam substrates may be formed by pyrolyzing an open-cell, polymer foam. During step 102 of method 100, the RVC foam substrate may have a bulk shape (e.g., a block), a near-net shape (e.g., a solid hemisphere), or a net shape (e.g., a hollow hemisphere), for example.

Figure 2:
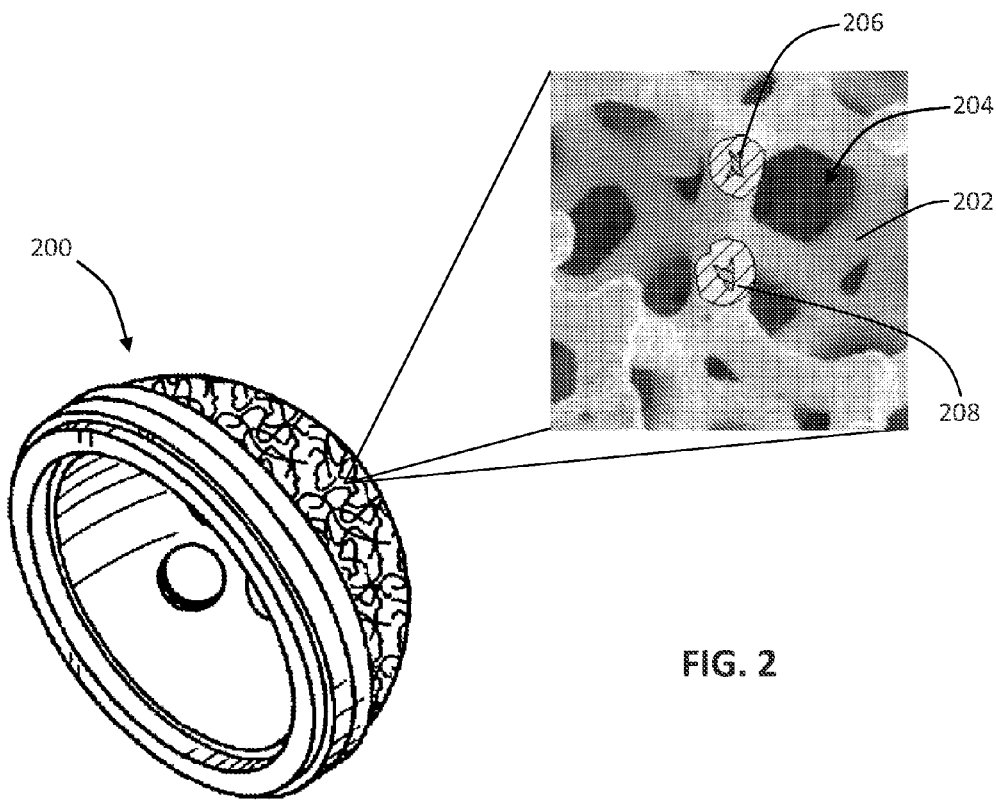
FIG. 2 is a perspective view of an orthopaedic implant manufactured according to the method of FIG. 1, the orthopaedic implant being formed of a highly porous material.

Continuing to step 104 of method 100 (FIG. 1), the ligaments of the porous substrate are coated with a thin film of biocompatible metal. With reference to FIG. 2, for example, the vitreous carbon ligaments 206 of the porous substrate are coated with a thin film of biocompatible metal 208. In this manner, the underlying porous substrate serves as a skeleton for the biocompatible metal coating.

In an exemplary embodiment of the present disclosure, tantalum or an alloy thereof is used to coat the porous substrate during the coating step 104 of method 100 (FIG. 1). Other suitable biocompatible metals that may be used to coat the porous substrate include other refractory (Group IV-VI) metals, such as titanium, niobium, hafnium, tungsten, and alloys thereof, for example. Such refractory metals generally retain their mechanical strength at high temperatures and have a high affinity for interstitial elements, including oxygen.

Also in an exemplary embodiment of the present disclosure, a chemical vapor deposition (CVD) process is performed to coat the porous substrate during the coating step 104 of method 100 (FIG. 1). An exemplary CVD process is described in the above-incorporated U.S. Pat. No. 5,282,861 to Kaplan.

Figure 3:
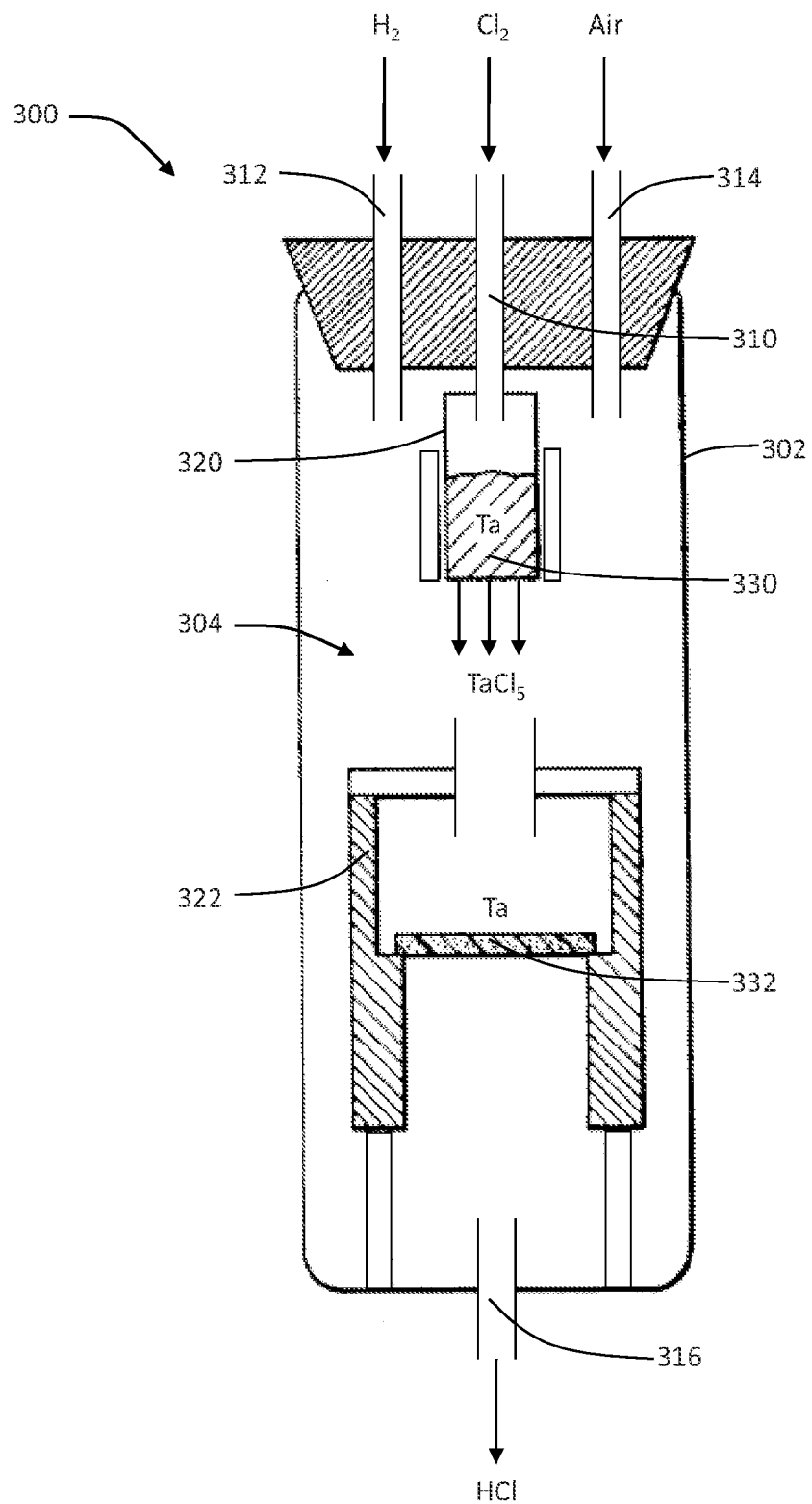
FIG. 3 is a schematic diagram of a chemical vapor deposition apparatus used to perform the method of FIG. 1.

With reference to FIG. 3, apparatus 300 is provided to perform the CVD process. FIG. 3 is schematic in nature, and it is understood that the design of apparatus 300 may vary. Apparatus 300 includes housing 302 that defines an internal reaction chamber 304. Apparatus 300 includes a chlorine ($Cl_2$) gas input 310, a hydrogen ($H_2$) gas input 312, and an air input 314 into reaction chamber 304, each having a suitable flow control valve (not shown). Apparatus 300 also includes an exhaust gas output 316 from reaction chamber 304. Within reaction chamber 304, apparatus 300 includes a heated chlorination chamber 320 and a heated deposition chamber or furnace 322. A supply of tantalum 330 or another biocompatible metal is located within chlorination chamber 320, and a porous substrate 332 is located within deposition chamber 322.

In operation, $Cl_2$ gas is injected via input 310 and $H_2$ gas is injected via input 312 into reaction chamber 304, which may be held under vacuum at a pressure of 1.0 to 2.0 Torr. Once inside the heated chlorination chamber 320, which may be resistance-heated to a temperature of approximately 500° C., the $Cl_2$ gas reacts with tantalum 330 to form tantalum chloride gas, such as $TaCl_5$ gas. The $TaCl_5$ gas then mixes with the injected $H_2$ gas and travels into the heated deposition chamber 322, which may be induction-heated to a temperature of approximately 900° C.-1,100° C., and more specifically to a temperature of approximately 900° C.-970° C. Once inside the heated deposition chamber 322, the $TaCl_5$ and $H_2$ gases flow around and into the porous substrate 332. Then, upon contact with the heated surfaces of porous substrate 332, the $TaCl_5$ and $H_2$ gases react to deposit tantalum metal and to liberate hydrogen chloride (HCl) gas. As shown in FIG. 2, the liberated tantalum metal is deposited as a thin, substantially uniform film 208 onto exterior and interior vitreous carbon ligaments 206 of the porous substrate. The HCl gas is then exhausted via exhaust gas output 316 from reaction chamber 304, along with excess reactant gases.

To promote even metal deposition and infiltration, the porous substrate 332 may be flipped and/or rotated in apparatus 300 during the CVD process or between individual cycles of the CVD process. Also, porous substrate 332 may be moved to different locations in apparatus 300, especially when multiple porous substrates 332 are coated simultaneously in apparatus 300. For example, when apparatus 300 contains a stack of porous substrates 332, a certain substrate may be located on top of the stack during a first CVD cycle and then may be moved to the bottom of the stack during a second CVD cycle.

Returning to FIG. 2, the above-described CVD process produces orthopaedic implant 200 having a large plurality of ligaments 202 that define open-cells or pores 204 therebetween, with each ligament 202 including a vitreous carbon core 206 covered by a thin film of deposited metal 208. Orthopaedic implant 200 is a highly porous structure having a porosity as low as 55%, 65%, or 75% and as high as 80% or 85%. The open-cells or pores 204 between ligaments 202 of orthopaedic implant 200 form a matrix of continuous channels having no dead ends, such that growth of cancellous bone, cells, and soft tissue through the structure is uninhibited. The highly porous structure is also lightweight, strong, and substantially uniform and consistent in composition.

The highly porous structure may be made in a variety of densities in order to selectively tailor orthopaedic implant 200 for particular applications. In particular, as discussed in the above-incorporated U.S. Pat. No. 5,282,861 to Kaplan, the highly porous structure may be fabricated to virtually any desired porosity and pore size, and can thus be matched with the surrounding natural bone in order to provide an optimized matrix for bone ingrowth and mineralization.

To achieve targeted mechanical properties, specifically a targeted compressive strength and a targeted ductility, the deposited metal film 208 on orthopaedic implant 200 may be micro-alloyed with controlled amounts of certain interstitial elements. In certain embodiments, the deposited metal film 208 on orthopaedic implant 200 may be micro-alloyed with controlled amounts of nitrogen, oxygen, and/or hydrogen. Such micro-alloying may occur during the above-described CVD process by controlling the relative amounts of $Cl_2$ gas delivered via input 310, $H_2$ gas delivered via input 312, and air delivered via input 314 (FIG. 3). Suitable gas flow rates are set forth in Table 1 below.

TABLE 1

| Input Gas | Flow Rate Range (sccm) |
|---|---|
| Chlorine ($Cl_2$) | 600-984 sccm |
| Hydrogen ($H_2$) | 1150-2200 sccm |
| Air | |

TABLE 1-continued

| Input Gas | Flow Rate Range (sccm) |
|---|---|
| Atmospheric Air (Nitrogen ($N_2$) and Oxygen ($O_2$)) or Pure or Substantially Pure $N_2$ | 10-40 sccm |

According to an exemplary embodiment of the present disclosure, the deposited metal film 208 on orthopaedic implant 200 is micro-alloyed according to Table 2 below. In this embodiment, the minimum nitrogen concentration of 488 ppm may ensure that orthopaedic implant 200 has sufficient compressive strength, while the maximum oxygen concentration of 1,212 ppm may ensure that orthopaedic implant 200 has sufficient ductility. The balance may include primarily tantalum and other elements such as iron, tungsten, molybdenum, silicon, and nickel, for example.

TABLE 2

| Element | Minimum Concentration (ppm (w/v)) | Maximum Concentration (ppm (w/v)) |
|---|---|---|
| Nitrogen | 488 | 2,200 |
| Oxygen | 0 | 1,212 |
| Hydrogen | 0 | 500 |

According to another exemplary embodiment of the present disclosure, the deposited metal film 208 of orthopaedic implant 200 is micro-alloyed according to Table 3 below. In this embodiment, the minimum nitrogen concentration of 488 ppm may ensure that orthopaedic implant 200 has sufficient compressive strength, while the maximum nitrogen concentration of 1,243 ppm may ensure that orthopaedic implant 200 has sufficient ductility. The balance may include primarily tantalum and other elements such as iron, tungsten, molybdenum, silicon, and nickel, for example.

TABLE 3

| Element | Minimum Concentration (ppm (w/v)) | Maximum Concentration (ppm (w/v)) |
|---|---|---|
| Nitrogen | 488 | 1,243 |
| Oxygen | 0 | 2,000 |
| Hydrogen | 0 | 500 |

In practice, limiting the oxygen concentration to 1,212 ppm (Table 2) may be more reasonable than limiting the nitrogen concentration to 1,243 ppm (Table 3). With reference to FIG. 3, the present inventors believe that a significant portion of any $O_2$ gas that is introduced into reaction chamber 304 via air input 314 may react with other process gases in reaction chamber 304, rather than depositing onto porous substrate 332. For example, a significant portion of any $O_2$ gas that is introduced via air input 314 may react with the $H_2$ gas that is introduced via $H_2$ gas input 312 to form water ($H_2O$) vapor. Therefore, during the CVD process, oxygen deposition onto porous substrate 332 may be minimal. Also, after the CVD process, oxygen deposition may be minimized by ensuring that the coated, porous substrate 332 is cooled before being removed from reaction chamber 304 and exposed to the atmosphere, because a warm part may undergo more oxidation than a cool part.

The concentration of oxygen in the deposited metal film 208 may be as low as 0 ppm (Table 2 and Table 3). Therefore, as indicated in Table 1 above, it is within the scope of the present disclosure that the air delivered via input 314 (FIG. 3) may comprise pure or substantially pure $N_2$ gas, rather than atmospheric air which contains $O_2$ gas in addition to $N_2$ gas. Even when the concentration of oxygen in the deposited metal film 208 is as low as 0 ppm, orthopaedic implant 200 may achieve the targeted compressive strength and the targeted ductility.

The chemical composition of orthopaedic implant 200 may be analyzed using a suitable chemical determinator to ensure compliance with Table 2 or Table 3. An exemplary chemical determinator is the TCH600 Series Nitrogen/Oxygen/Hydrogen Determinator, which is commercially available from LECO Corportation of St. Joseph, Mich. The chemical determinator may operate based on fusion in an inert, high-temperature environment and may include infrared (IR) and thermal conductivity (TC) detectors to detect nitrogen, oxygen, and hydrogen in the material.

Micro-alloying the deposited metal film 208 on orthopaedic implant 200 may ensure that orthopaedic implant 200 has a specific compressive strength (SCS) of at least 24,000 psi, for example. In an exemplary embodiment of the present disclosure, SCS is determined by subjecting orthopaedic implant 200 to an increasing compressive strain. The applied compressive strain may be increased incrementally until, at a maximum compressive load, 0.04" of total displacement occurs or compressive failure occurs, for example. SCS may be calculated by dividing the ultimate compressive strength (UCS) of the material by the relative density (% RD) of the material, where the UCS equals the maximum compressive load divided by the cross-sectional area of the material. For example, a material having a relative density of 16% RD and a cross-sectional area of 0.13 square inches that withstands a maximum compressive load of 1,300 lbf would have a calculated SCS of 62,500 psi. SCS may be determined using a suitable mechanical testing apparatus, such as the Instron 5567 Universal Testing Instrument, which is commercially available from Instron of Norwood, Mass.

Also, micro-alloying the deposited metal film 208 on orthopaedic implant 200 may ensure that orthopaedic implant 200 has a ductility of at least 50%, for example. In an exemplary embodiment of the present disclosure, ductility is determined by subjecting orthopaedic implant 200 to an increasing compressive strain and measuring the percent reduction in compressive load. If the compressive load decreases by more than 50% of its maximum value, the material may be deemed too brittle. The ductility of the material may be determined using a suitable mechanical testing apparatus, such as the above-described Instron 5567 Universal Testing Instrument.

By micro-alloying orthopaedic implant 200 and achieving certain targeted mechanical properties, the material may be densified to a relative density less than 18% RD. For example, the material may be densified to a relative density as low as 12% RD, 13% RD, or 14% RD and as high as 15% RD, 16% RD, or 17% RD, or within any range delimited by any pair of the forgoing values. For purposes of the present disclosure, the relative density of a given piece of material is calculated by dividing the actual density of the piece of material by the theoretical density of the deposited metal and multiplying by 100 to express the ratio as a percentage. When the deposited metal is tantalum having a theoretical density of 16.6 $g/cm^3$, the piece of material may have an actual density less than 2.9 $g/cm^3$ or less than 3.0 $g/cm^3$ (to arrive at less than 18% RD). For example, the piece of material may have an actual density as low as 2.0 $g/cm^3$ (to arrive at 12% RD), 2.2 $g/cm^3$ (to arrive at 13% RD), or 2.3 $g/cm^3$ (to arrive at 14% RD) and as high as 2.5 $g/cm^3$ (to arrive at 15% RD), 2.7 $g/cm^3$ (to arrive at 16%

RD), or 2.8 g/cm³ (to arrive at 17% RD). Although the underlying porous substrate and interstitial elements would contribute to the weight of the material, those contributions are insignificant and may be ignored such that the material is assumed to be entirely metal when calculating the relative density.

The ability to reduce the relative density of the material may decrease the time required to manufacture the material. If the material is required to have a relative density of 18% RD, for example, the CVD process would continue until the material reaches a relatively high target weight. In certain embodiments, 8 cycles, 10 cycles, or 12 cycles of the CVD process may be required, with each individual cycle lasting more than 10 hours. However, if the material is able to have a relative density of 12% RD, for example, the CVD process may terminate when the material reaches a relatively low target weight. In certain embodiments, the CVD process may be shortened by 10 hours, 20 hours, 30 hours, or more. Such time savings may be recognized while still achieving certain targeted mechanical properties.

Additionally, the ability to reduce the relative density of the material may decrease the inputs and ingredients required to manufacture the material. If the material is required to have a relative density of 18% RD, for example, a relatively large amount of tantalum metal would be required to produce a relatively thick coating on the porous substrate. However, if the material is able to have a relative density of 12% RD, for example, less tantalum metal would be required to produce a relatively thin coating on the porous substrate. Such material savings may be recognized while still achieving certain targeted mechanical properties.

At this stage, because the material is expected to achieve targeted mechanical properties for implantation, the material is considered to be densified to a "completed extent." As used herein, the "completed extent" of densification means that the material need not be further densified or coated before implantation. The material may remain permanently at the "completed extent" of densification, not just temporarily between coating cycles, for example. In this respect, the "completed extent" of densification is not an intermediate extent of densification between coating cycles. Also, the material may be provided to another party or otherwise prepared for implantation in the "completed extent" without requiring additional coating cycles.

After the material is densified to the "completed extent" during the coating step 104 of method 100 (FIG. 1), orthopaedic prosthesis 200 may be subjected to any necessary shaping, processing, sterilizing, or packaging steps. For example, a polymeric bearing component may be secured onto orthopaedic prosthesis 200 to form an articulating, joint replacement implant. Exemplary methods for attaching a polymeric bearing component to a highly porous material are described in U.S. Patent Application Publication No. 2009/0112315 to Fang et al., the entire disclosure of which is expressly incorporated herein by reference. As another example, orthopaedic prosthesis 200 may be coupled to a solid metal substrate, such as by sintering or diffusion bonding. Exemplary methods for attaching a highly porous material to a solid metal substrate are described in U.S. Pat. No. 7,918,382 to Charlebois et al. and in U.S. Pat. No. 7,686,203 to Rauguth et al., the entire disclosures of which are expressly incorporated herein by reference.

Finally, in step 106 of method 100 (FIG. 1), orthopaedic prosthesis 200 is implanted into a patient's body. The illustrative orthopaedic implant 200 of FIG. 2 is hemispherical in shape and is configured to be implanted into the patient's hip joint as a prosthetic acetabular component. It is also within the scope of the present disclosure that orthopaedic implant 200 may be a prosthetic proximal femoral component for use in the patient's hip joint, a prosthetic distal femoral component for use in the patient's knee joint, a prosthetic tibial component for use in the patient's knee joint, a prosthetic humeral component for use in the patient's shoulder joint, a prosthetic dental component, or a prosthetic spinal component, for example. Orthopaedic implant 200 may also be in the shape of a plate, plug, or rod, for example.

EXAMPLES

The following examples illustrate the impact of microalloying a highly porous tantalum structure.

1. Example 1 a. Design of Experiment

A first experiment was designed and performed to evaluate the SCS of a highly porous tantalum structure based on two factors: (1) the ratio of atmospheric air flow rate to chlorine flow rate introduced to the CVD process, and (2) the final relative density.

The test samples were RVC cylinders having nominal dimensions of 0.400" in length and 0.400" in diameter. When coating the samples, the air/chlorine ratio was varied between 0.00 and 0.10, and the final relative density of the samples was varied between about 18% RD and about 22% RD. Other CVD process parameters remained constant throughout the experiment, as set forth in Table 4 below.

TABLE 4

| CVD Process Parameter | Setpoint |
| --- | --- |
| Chlorine ($Cl_2$) Gas Flow Rate | 900 sccm |
| Hydrogen ($H_2$) Gas Flow Rate | 1800 sccm |
| Chlorination Chamber Temperature | 500° C. |
| Deposition Chamber Temperature | 900° C. |
| Vacuum Pressure | 1.6 Torr |
| Cycle Duration | 600 minutes |

Each test sample was removed from the CVD apparatus after reaching a target weight (about 2.4-3.2 grams) corresponding to its specified relative density. Due to the nature of the CVD process, variations of ±1% RD, and in certain cases ±1.5% RD, from the specified relative densities were deemed acceptable.

The samples were subjected to mechanical testing to measure SCS (psi) and were subjected to chemical testing to measure the nitrogen concentration (ppm) and the oxygen concentration (ppm) in the samples. Such testing methods are described further above.

b. Effect of Relative Density on SCS

Because SCS is effectively normalized for relative density, by definition, relative density did not have a statistically significant effect on SCS. A reduced statistical model was created by removing the relative density factor, as well as the interaction between the air/chlorine ratio factor and the relative density factor.

c. Effect of Air/Chlorine Ratio on SCS

Analysis of the reduced model indicated with high probability ($p=0.003$) that the air/chlorine ratio accounts for 98.5% of the variation in average SCS. Regression analysis of the data resulted in the following best-fit ($R^2=0.8997$), exponential relationship between SCS and the air/chlorine ratio:

$$SCS(psi)=18{,}392 e^{[12.41(\text{Air Flow Rate(sccm)}/\text{Chlorine Flow Rate(sccm)})]} \quad \text{Equation 1}$$

According to Equation 1 above, strength may be improved by increasing the air/chlorine ratio during the CVD process. However, increasing the air/chlorine ratio too much could lead to brittle failure. Although none of the samples in the present study exhibited brittle failure during compressive testing, one sample that was manufactured at the highest air/chlorine ratio (0.10) exhibited material separation when subjected to repeated compressive tests, which may indicate the onset of brittle failure.

d. Effect of Air/Chlorine Ratio on Nitrogen Concentration

Analysis of the reduced model indicated with high probability (p=0.002) that the air/chlorine ratio accounts for 98.1% of the variation in the average nitrogen concentration. Regression analysis of the data resulted in the following best-fit ($R^2$=0.9738), exponential relationship between the air/chlorine ratio and the average nitrogen concentration:

$$\text{Nitrogen Concentration(ppm)}=209.88e^{\wedge}[21.748(\text{Air Flow Rate(sccm)}/\text{ChlorineFlowRate(sccm)})] \quad \text{Equation 2}$$

e. Effect of Air/Chlorine Ratio on Oxygen Concentration

The data indicated that the average oxygen concentration is independent of relative density, but the average oxygen concentration reached a maximum at the center point for relative density (20% RD). Similarly, the data also indicated that the average oxygen concentration is independent of the air/chlorine ratio, but the average oxygen concentration reached a maximum at the center point for the air/chlorine ratio (0.05).

Neither the air/chlorine ratio, the relative density, nor the interaction between the air/chlorine ratio and the relative density had a statistically significant effect on the standard deviation of the oxygen concentration. Regression analysis of the data indicated no significant statistical relationship ($R^2$=0.0012) between the air/chlorine ratio and the average oxygen concentration.

$N_2$ and $O_2$ gases are both introduced proportionally into the CVD reaction chamber in the incoming atmospheric air stream, so the present inventors originally anticipated that the relationship between the air/chlorine ratio and the average oxygen concentration in the samples would be similar to the relationship between the air/chlorine ratio and the average nitrogen concentration in the samples (Equation 2). The present inventors now believe, however, that a significant portion of the introduced $O_2$ gas reacts with other process gases in the chamber, rather than depositing onto the porous substrate. For example, the introduced $O_2$ gas may react with the introduced $H_2$ gas to form water ($H_2O$) vapor.

f. Effect of Nitrogen Concentration on SCS

Given the high correlation between the air/chlorine ratio and SCS (Equation 1) and the high correlation between the air/chlorine ratio and the average nitrogen concentration (Equation 2), the inventors anticipated a high correlation between SCS and the average nitrogen concentration. Regression analysis of the data resulted in the following best-fit ($R^2$=0.9697), linear relationship between SCS and the average nitrogen concentration:

$$\text{SCS(psi)}=10,309+33.681*(\text{Nitrogen Concentration (ppm)}) \quad \text{Equation 3}$$

According to Equation 3 above, micro-alloying a highly porous tantalum material with nitrogen is a potential mechanism for increasing SCS.

Although regression analysis indicated a high correlation between SCS and the average nitrogen concentration (Equation 3), regression analysis did not indicate a statistically significant correlation ($R^2$=0.0469) between SCS and the average oxygen concentration.

2. Example 2 a. Design of Experiment

A second experiment was designed and performed to evaluate the SCS and the ductility of a highly porous tantalum structure based on the concentration of nitrogen and oxygen in the structure.

The test samples were RVC cylinders having nominal dimensions of 0.400" in length and 0.400" in diameter. A two-step CVD process was performed according to Table 5 below to produce coated samples having nitrogen concentrations between about 350 ppm and about 1,200 ppm, oxygen concentrations between about 300 ppm and about 1,200 ppm, and relative densities between about 12% RD and about 18% RD.

TABLE 5

| CVD Process Parameter | Operating Range |
|---|---|
| Step 1 | |
| Chlorine ($Cl_2$) Gas Flow Rate | 600-984 sccm |
| Hydrogen ($H_2$) Gas Flow Rate | 1,150-2,200 sccm |
| Atmospheric Air Flow Rate | 10-40 sccm |
| Chlorination Chamber Temperature | 500° C. |
| Deposition Chamber Temperature | 900-970° C. |
| Vacuum Pressure | 1.6 Torr |
| Total Duration | 5,500-7,500 minutes |
| Step 2 | |
| Chlorine ($Cl_2$) Gas Flow Rate | 0 sccm |
| Hydrogen ($H_2$) Gas Flow Rate | 0 sccm |
| Atmospheric Air Flow Rate | 15-45 sccm |
| Deposition Chamber Temperature | 485-515° C. |
| Vacuum Pressure | 1.0 Torr |
| Total Duration | 120-150 minutes |

The samples were subjected to mechanical testing to measure SCS (psi) and ductility (%) and were subjected to chemical testing to measure the nitrogen concentration (ppm), the oxygen concentration (ppm), and the hydrogen concentration (ppm) in the samples. Such testing methods are described further above.

b. Correlation between Nitrogen and Oxygen Concentrations

Analysis of the data indicated no statistically signification correlation (p=0.298, a=0.05) between nitrogen and oxygen concentrations in the samples. Thus, the effects of nitrogen and oxygen concentrations may be evaluated separately.

c. Effect of Relative Density on Nitrogen and Oxygen Concentrations

Analysis of the data indicated no statistically signification correlation between relative density and the nitrogen concentrations in the samples (p=0.186, a=0.05) or between relative density and the oxygen concentrations in the samples (p=0.303, a=0.05). Thus, relative density may be discounted when analyzing the effects of nitrogen and oxygen concentrations.

d. Effect of Nitrogen and Oxygen Concentrations on SCS

Regression analysis of the data resulted in the following best-fit ($R^2$=0.861), linear relationship between SCS and the average nitrogen and oxygen concentrations:

$$\text{SCS(psi)}=11,361+38.3*(\text{Nitrogen Concentration (ppm)})+11.2*(\text{Oxygen Concentration(ppm)}) \quad \text{Equation 4}$$

The entire Equation 4 was found to be statistically significant (p=0.000, a=0.05). Also, each individual term within Equation 4—the constant term (p=0.001, a=0.05), the nitrogen concentration term (p=0.000, a=0.05), and the oxygen concentration term (p=0.012, a=0.05)—was found to be statistically significant.

According to Equation 4, increasing the concentration of nitrogen and/or oxygen increases SCS because both signs are positive. Also, the nitrogen concentration has a larger effect on SCS than the oxygen concentration because the nitrogen concentration term is larger in magnitude than the oxygen concentration term. A certain minimum nitrogen concentration or a certain minimum oxygen concentration may ensure SCS above the specified minimum of 24,000 psi, for example.

Regression analysis of the data resulted in the following best-fit ($R^2$=0.147), linear relationship between SCS and the average oxygen concentration alone:

$$SCS(psi)=33,973+21.27*(Oxygen\ Concentration\ (ppm)) \quad \text{Equation 5}$$

Also, regression analysis of the data resulted in the following best-fit ($R^2$=0.832), linear relationship between SCS and the average nitrogen concentration alone:

$$SCS(psi)=16,308+40.17*(Nitrogen\ Concentration\ (ppm)) \quad \text{Equation 6}$$

Figure 4A:
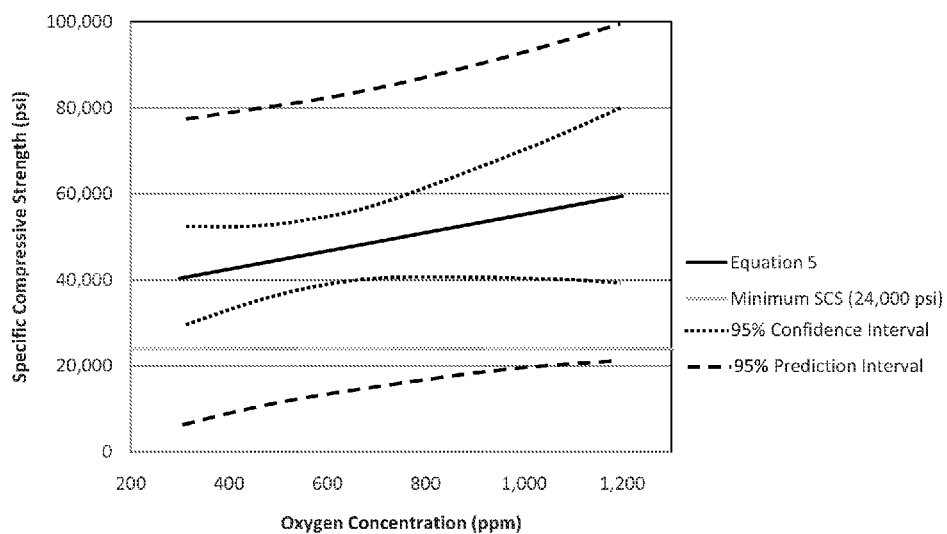
FIG. 4A is an experimental graphical representation of the specific compressive strength of the highly porous material based on the concentration of oxygen in the material.
Figure 4B:
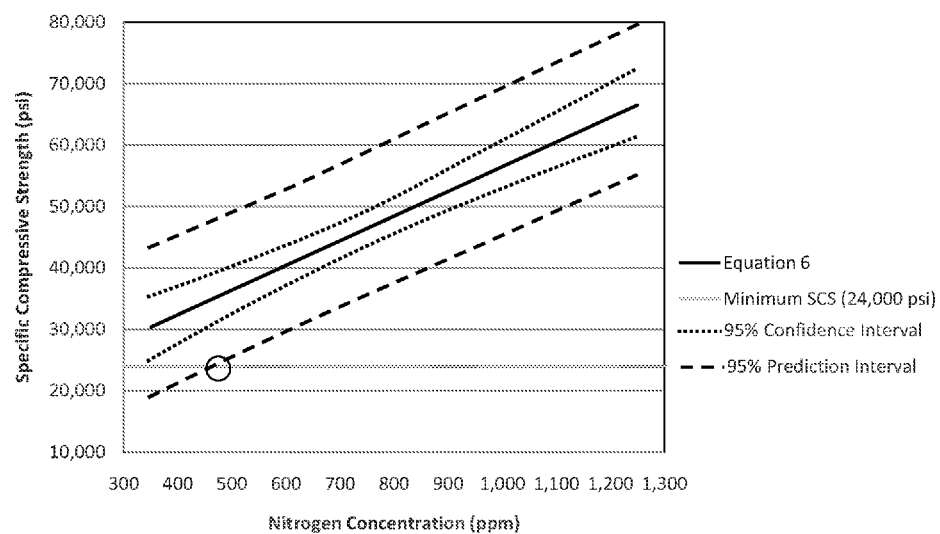
FIG. 4B is an experimental graphical representation of the specific compressive strength of the highly porous material based on the concentration of nitrogen in the material.

Equations 5 and 6 are plotted in FIGS. 4A and 4B, respectively, along with 95% prediction intervals and 95% confidence intervals. For any chosen oxygen concentration value along the x-axis of FIG. 4A, the vertical distance between the prediction interval lines represents the effect of varying the nitrogen concentration while holding the oxygen concentration constant. Similarly, for any chosen nitrogen concentration value along the x-axis of FIG. 4B, the vertical distance between the prediction interval lines represents the effect of varying the oxygen concentration while holding the nitrogen concentration constant.

With respect to FIG. 4A, the lower 95% prediction interval for oxygen is consistently below the specified minimum SCS of 24,000 psi. Thus, no minimum oxygen concentration within the tested range of about 300 ppm and about 1,200 ppm would ensure SCS of at least 24,000 psi with 95% confidence.

With respect to FIG. 4B, the lower 95% prediction interval for nitrogen intersects the 24,000 psi reference line at a nitrogen concentration of 488 ppm (see circled intersection point in FIG. 4B). Thus, even in the absence of oxygen, a nitrogen concentration of at least 488 ppm would ensure SCS of at least 24,000 psi with 95% confidence.

e. Effect of Nitrogen and Oxygen Concentrations on Ductility

Regression analysis of the data resulted in the following best-fit ($R^2$=0.505), linear relationship between ductility and the average nitrogen and oxygen concentrations:

$$Ductility(\%)=1.09-0.000203*(Nitrogen\ Concentration(ppm))-0.000150*(Oxygen\ Concentration\ ppm)) \quad \text{Equation 7}$$

The entire Equation 7 was found to be statistically significant (p=0.000, a=0.05). Also, each individual term within Equation 7—the constant term (p=0.000, a=0.05), the nitrogen concentration term (p=0.000, a=0.05), and the oxygen concentration term (p=0.022, a=0.05)—was found to be statistically significant.

According to Equation 7, increasing the concentration of nitrogen and/or oxygen decreases ductility because both signs are negative. A certain maximum nitrogen concentration or a certain maximum oxygen concentration may ensure ductility above the specified minimum of 50%, for example.

Regression analysis of the data resulted in the following best-fit ($R^2$=0.217), linear relationship between ductility and the average oxygen concentration alone:

$$Ductility(\%)=0.9721-0.000204*(Oxygen\ Concentration(ppm)) \quad \text{Equation 8}$$

Also, regression analysis of the data resulted in the following best-fit ($R^2$=0.430), linear relationship between ductility and the average nitrogen concentration alone:

$$Ductility(\%)=1.026-0.000228*(Nitrogen\ Concentration(ppm)) \quad \text{Equation 9}$$

Figure 5A:
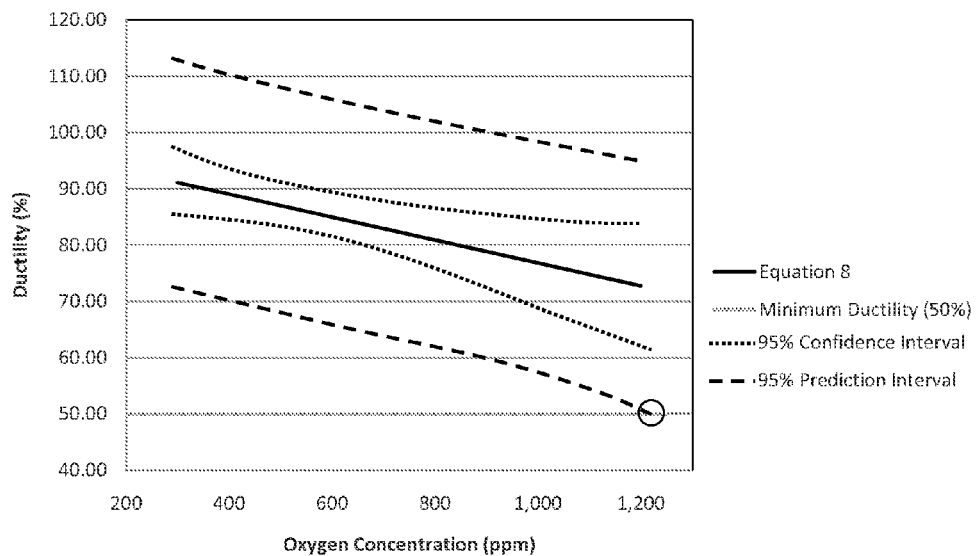
FIG. 5A is an experimental graphical representation of the ductility of the highly porous material based on the concentration of oxygen in the material.
Figure 5B:
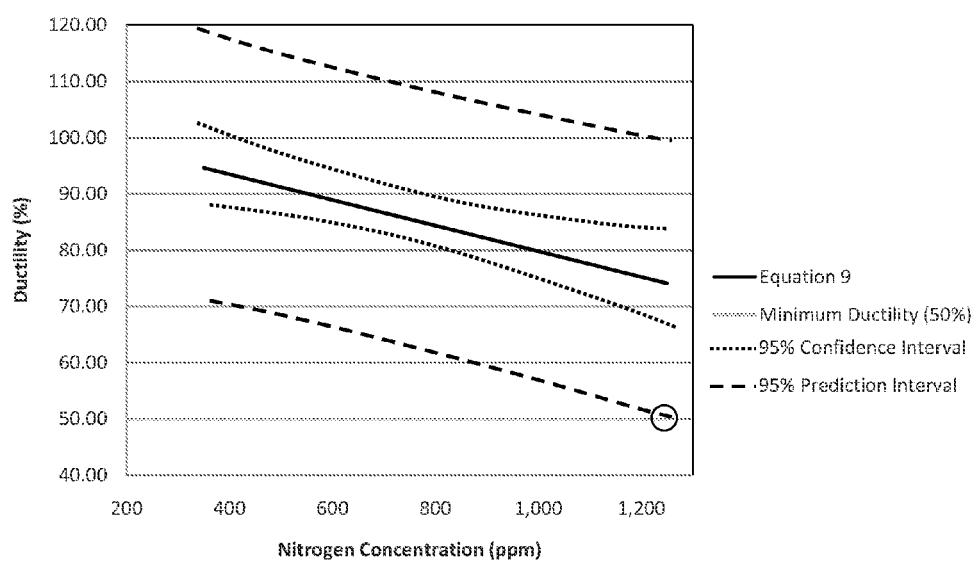
FIG. 5B is an experimental graphical representation of the ductility of the highly porous material based on the concentration of nitrogen in the material.

Equations 8 and 9 are plotted in FIGS. 5A and 5B, respectively, along with 95% prediction intervals and 95% confidence intervals. For any chosen oxygen concentration value along the x-axis of FIG. 5A, the vertical distance between the prediction interval lines represents the effect of varying the nitrogen concentration while holding the oxygen concentration constant. Similarly, for any chosen nitrogen concentration value along the x-axis of FIG. 5B, the vertical distance between the prediction interval lines represents the effect of varying the oxygen concentration while holding the nitrogen concentration constant.

With respect to FIG. 5A, the lower 95% prediction interval for oxygen intersects the 50% reference line at an oxygen concentration of 1,212 ppm (see circled intersection point in FIG. 5A). Thus, even in the presence of maximum nitrogen, an upper limit oxygen concentration of 1,212 ppm would ensure ductility of at least 50% with 95% confidence.

With respect to FIG. 5B, the lower 95% prediction interval for nitrogen intersects the 50% reference line at a nitrogen concentration of 1,243 ppm (see circled intersection point in FIG. 5B). Thus, even in the presence of maximum oxygen, an upper limit nitrogen concentration of 1,243 ppm would ensure ductility of at least 50% with 95% confidence.

While this invention has been described as having exemplary designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A highly porous biomaterial configured to be implanted in a patient's body, the highly porous biomaterial comprising:
 a porous substrate having a plurality of ligaments that define pores of the porous substrate; and
 a biocompatible metal coating applied to the plurality of ligaments of the porous substrate, the biocompatible metal of the coating having a minimum nitrogen concentration of 488 ppm, the highly porous biomaterial having a relative density less than 18% and a specific compressive strength of at least 24,000 psi, the relative density being a percentage obtained by dividing an actual density of the highly porous biomaterial by a theoretical density of the biocompatible metal of the coating.

2. The highly porous biomaterial of claim 1, wherein the highly porous biomaterial has a relative density of at least 12% and less than 18%.

3. The highly porous biomaterial of claim 1, wherein the highly porous biomaterial has a ductility of at least 50%.

4. The highly porous biomaterial of claim 1, wherein the porous substrate comprises reticulated vitreous carbon.

5. The highly porous biomaterial of claim 1, wherein the biocompatible metal of the coating comprises tantalum, the theoretical density of tantalum being 16.6 g/cm$^3$.

6. The highly porous biomaterial of claim 5, wherein the actual density of the highly porous biomaterial is 3.0 g/cm$^3$ or less.

7. The highly porous biomaterial of claim 1, wherein the biocompatible metal of the coating has a minimum oxygen concentration of 0 ppm.

8. The highly porous biomaterial of claim 1, wherein the biocompatible metal of the coating has a maximum nitrogen concentration of 1,243 ppm.

9. The highly porous biomaterial of claim 8, wherein the biocompatible metal of the coating has a maximum oxygen concentration of 2,000 ppm.

10. The highly porous biomaterial of claim 1, wherein the biocompatible metal of the coating has a maximum oxygen concentration of 1,212 ppm.

11. The highly porous biomaterial of claim 10, wherein the biocompatible metal of the coating has a maximum nitrogen concentration of 2,200 ppm.

12. The highly porous biomaterial of claim 1, wherein the biocompatible metal of the coating has a maximum hydrogen concentration of 500 ppm.

13. An orthopaedic implant made at least in part of the highly porous biomaterial of claim 1.

14. The highly porous biomaterial of claim 1, wherein the highly porous biomaterial is formed by a method of manufacturing comprising:
    providing the porous substrate having the plurality of ligaments that define the pores of the porous substrate;
    depositing the biocompatible metal coating onto the plurality of ligaments of the porous substrate; and
    setting at least one of:
        a maximum oxygen concentration in the metal coating at 1,212 ppm; and
        a maximum nitrogen concentration in the metal coating at 1,243 ppm.

15. The highly porous biomaterial of claim 14, wherein the setting provides the highly porous biomaterial with a specific compressive strength of at least 24,000 psi.

16. The highly porous biomaterial of claim 14, wherein the method further comprises setting a minimum nitrogen concentration in the metal coating at 488 ppm.

17. The highly porous biomaterial of claim 1, wherein the highly porous biomaterial is formed by a method of manufacturing comprising:
    providing the porous substrate having the plurality of ligaments that define the pores of the porous substrate;
    depositing the biocompatible metal coating onto the plurality of ligaments of the porous substrate; and
    setting a minimum nitrogen concentration in the metal coating at 488 ppm.

18. The highly porous biomaterial of claim 17, wherein the setting provides the highly porous biomaterial with a ductility of at least 50%.

19. The highly porous biomaterial of claim 17, wherein the method further comprises setting at least one of:
    a maximum oxygen concentration in the metal coating at 1,212 ppm; and
    a maximum nitrogen concentration in the metal coating at 1,243 ppm.

20. The highly porous biomaterial of claim 1, wherein the highly porous biomaterial is formed by a method of manufacturing comprising:
    providing the porous substrate having the plurality of ligaments that define the pores of the porous substrate; and
    depositing the biocompatible metal coating onto the plurality of ligaments of the porous substrate to a completed extent, the highly porous biomaterial having a relative density less than 18% at the completed extent, the relative density being a percentage obtained by dividing an actual density of the highly porous biomaterial by a theoretical density of the biocompatible metal of the coating.

21. The highly porous biomaterial of claim 20, wherein the method further comprises providing the highly porous biomaterial at the completed extent for implantation in a patient's body without depositing more of the biocompatible metal coating onto the plurality of ligaments.

22. The highly porous biomaterial of claim 20, wherein the highly porous biomaterial has a relative density of at least 12% and less than 18% at the completed extent.

* * * * *